(12) United States Patent
Yasuhara

(10) Patent No.: US 7,612,562 B2
(45) Date of Patent: Nov. 3, 2009

(54) MAGNETIC RESONANCE IMAGING APPARATUS, SETTING SUPPORTING APPARATUS, AND SETTING SUPPORTING METHOD

(75) Inventor: Yasutake Yasuhara, Nasushiobara (JP)

(73) Assignees: Kabushiki Kaisha Toshiba, Minato-Ku, Tokyo (JP); Toshiba Medical Systems Corporation, Otawara-shi, Tochigi (JP)

( * ) Notice: Subject to any disclaimer, the term of this patent is extended or adjusted under 35 U.S.C. 154(b) by 0 days.

(21) Appl. No.: 12/173,100

(22) Filed: Jul. 15, 2008

(65) Prior Publication Data

US 2009/0021257 A1 Jan. 22, 2009

(30) Foreign Application Priority Data

Jul. 18, 2007 (JP) ............................. 2007-187424

(51) Int. Cl.
    *G01V 3/00* (2006.01)
(52) U.S. Cl. ........................................ 324/318; 600/410
(58) Field of Classification Search ................. 324/318, 324/322; 600/410
    See application file for complete search history.

(56) References Cited

U.S. PATENT DOCUMENTS

| 5,525,905 | A | * | 6/1996 | Mohapatra et al. ........... 324/318 |
| 5,823,960 | A | * | 10/1998 | Young et al. ................. 600/415 |
| 6,023,636 | A | * | 2/2000 | Wendt et al. ................. 600/410 |
| 6,246,896 | B1 | * | 6/2001 | Dumoulin et al. ........... 600/411 |
| 6,421,551 | B1 | * | 7/2002 | Kuth et al. .................... 600/410 |
| 7,141,976 | B2 | * | 11/2006 | Campagna ................... 324/318 |
| 2004/0081341 | A1 | | 4/2004 | Cherek et al. |

* cited by examiner

*Primary Examiner*—Louis M Arana
(74) *Attorney, Agent, or Firm*—Nixon & Vanderhye PC

(57) ABSTRACT

Support information including at least a setting image showing a present configuration of placing a patient on a bed and a present configuration of placing an RF coil for the patient is displayed. As necessary, the support information is displayed while including the position of a virtual magnetic field center corresponding to the position of a magnetic field center in the case of moving the bed into a gantry. The displayed support information is stored at a predetermined timing and can be read arbitrarily. By observing the displayed support information, the operator can promptly and easily determine whether the placement configuration of the patient and that of the RF coil at present are proper or not, and can accurately correct the placement configuration of the patient or the RF coil.

15 Claims, 5 Drawing Sheets

MAGNETIC RESONANCE IMAGING APPARATUS, SETTING SUPPORTING APPARATUS, AND SETTING SUPPORTING METHOD

CROSS-REFERENCE TO RELATED APPLICATIONS

This application is based upon and claims the benefit of priority from prior Japanese Patent Application No. 2007-187424, filed Jul. 18, 2007, the entire contents of which are incorporated herein by reference.

BACKGROUND OF THE INVENTION

1. Field of the Invention

The present invention relates to a magnetic resonance imaging apparatus, a setting supporting apparatus, and a setting supporting method capable of providing information for supporting placement of a patient on a bed top board and placement of an RF coil for the patient in magnetic resonance imaging.

2. Description of the Related Art

The magnetic resonance imaging is an imaging method of magnetically exciting nuclear spins in a subject who is put in a magnetostatic field by an RF signal of the Larmor frequency, obtaining an MR signal generated in association with the excitation, and reconstructing an MRI image and an MRA image (hereinbelow, called MP images).

In the magnetic resonance imaging, an RF coil having a shape adapted to a region to be imaged (imaging region) is selected and disposed on the surface of the subject or near the subject. A subject is placed on the bed top board, and the RF coil is placed on the surface of the subject. After that, the imaging region is adjusted to a laser beam projection position of a laser projector disposed in the front face of a gantry of a magnetic resonance imaging apparatus. The imaging region is then sent to a magnetic field center (isocenter) in the center of the gantry by a bed horizontal moving mechanism of the magnetic resonance imaging apparatus.

If the RF coil is not placed in the optimum positional relation with the imaging region, a high-quality image cannot be obtained. Generally, placement of a subject and an RF coil in conventional magnetic resonance imaging is executed according to a method of placing an RF coil and the like described in an instruction manual or relying on the experience of the operator himself/herself.

However, the optimum coil placement position slightly varies depending on the body shapes of subjects and lesions to be imaged. Therefore, whether a subject or an RF coil can be placed properly or not (that is, whether an image of an imaging region can be acquired with high quality or not) depends on the coil setting skill of the operator. In some cases, the quality of a diagnosis image varies among operators.

For example, in the case of performing imaging to check the course of a treatment, it is preferable to place a coil in the same position as that in the previous time. It is, however, difficult even for the same operator to reproduce the placement of a subject and a coil of last time with high precision. It is more difficult for an operator to reproduce the placement of a subject and a coil performed by another operator.

Further, at the time of adjusting an imaging region to a laser projector, generally, the imaging region is moved by using a slow configuration of a bed horizontal moving mechanism to a magnetic field center position. During the bed horizontal movement, the operator has to visually observe the positions of a subject and an RF coil. Consequently, an artificial load is heavy.

BRIEF SUMMARY OF THE INVENTION

The present invention has been made in view of the circumstances, and an object of the invention is to provide a magnetic resonance imaging apparatus, a setting supporting apparatus, and a setting supporting method capable of facilitating a setting of a subject and an RF coil and reproducing a configuration of setting a subject and an RF coil in past image acquisition with high precision.

According to an aspect of the present invention, there is provided a magnetic resonance imaging apparatus comprising: a gantry which generates a magnetostatic field space; a bed which places a subject placed on a top board on the outside of the magnetostatic field space into the magnetostatic field space by moving the top board; an RF coil disposed on a surface of the subject or near the subject; an image capturing unit which acquires a setting image for showing a setting configuration of the subject placed on the top board on the outside of the magnetostatic field space and a setting configuration of the RF coil placed on the surface of the subject or near the subject; a support information generating unit which generates support information including at least the setting image and supporting at least one of a setting of the subject onto the top board and a setting of the RF coil; and a display unit which displays the support information.

According to another aspect of the present. invention, there is provided a magnetic resonance imaging apparatus comprising: a gantry having an opening into which a subject is inserted, a magnetostatic field magnet which generates a magnetostatic field space, and a gradient coil which generates a gradient magnetic field; a bed which inserts a top board on which the subject is mounted into the opening; an RF coil disposed on a surface of the subject or near the subject; an image capturing unit which acquires an image of the subject including the RF coil; a support information generating unit which generates a setting image showing a positional relation between the subject and the RF coil on the basis of information acquired by the image capturing unit in order to support a setting of the RF coil to the subject; and a display unit which displays the setting image.

According to yet another aspect of the present invention, there is provided a setting supporting apparatus for use in a magnetic resonance imaging apparatus which applies a uniform magnetostatic field to a subject, applies a high frequency magnetic field and a gradient magnetic field in accordance with a predetermined pulse sequence, and detects a magnetic resonance signal from the subject by an RF coil to acquire an image, the setting supporting apparatus comprising: an image capturing unit which acquires an image of the subject including the RF coil; a support information generating unit which generates a setting image showing a positional relation between the subject and the RF coil on the basis of information acquired by the image capturing unit in order to support a setting of the RF coil to the subject; and a display unit which displays the setting image.

According to yet another aspect of the present invention, there is provided a method of supporting a setting of an RF coil to a subject in magnetic resonance imaging, comprising: capturing an image of the subject mounted on a top board of a bed and an RF coil disposed on a surface of the subject or near the subject; generating a setting image showing a positional relation between the subject and the RF coil on the basis of information acquired by the image capturing in order to support the setting of the RF coil to the subject; and displaying the setting image.

According to yet another aspect of the present invention, there is provided a method of supporting a setting of an RF coil to a subject in magnetic resonance imaging, comprising: capturing an image of the subject mounted on a top board of a bed and an RF coil disposed on a surface of the subject or near the subject; generating a setting image showing a positional relation between the subject and the RF coil on the basis of information acquired by the image capturing in order to support the setting of the RF coil to the subject; generating support information for supporting a setting of the subject on the top board; and displaying the support information together with the setting image.

DETAILED DESCRIPTION OF THE INVENTION

Figure 1:
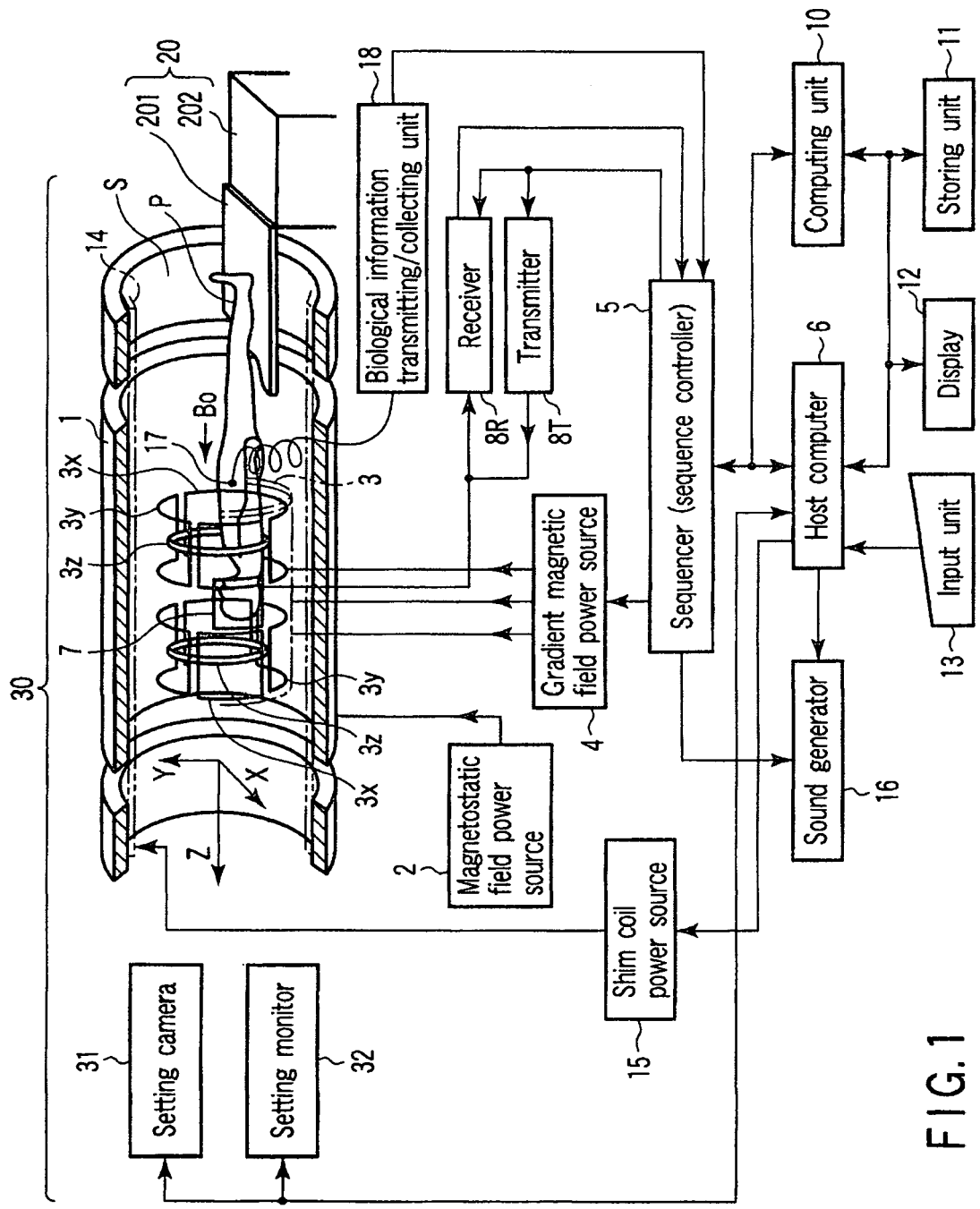
FIG. 1 is a block configuration diagram of a magnetic resonance imaging apparatus according to an embodiment of the invention.

Embodiments of the present invention will be described below with reference to the drawings. In the following description, the same reference numerals are designated to elements having substantially the same function and configuration, and repetitive description will be given only when necessary.

Figure 2:
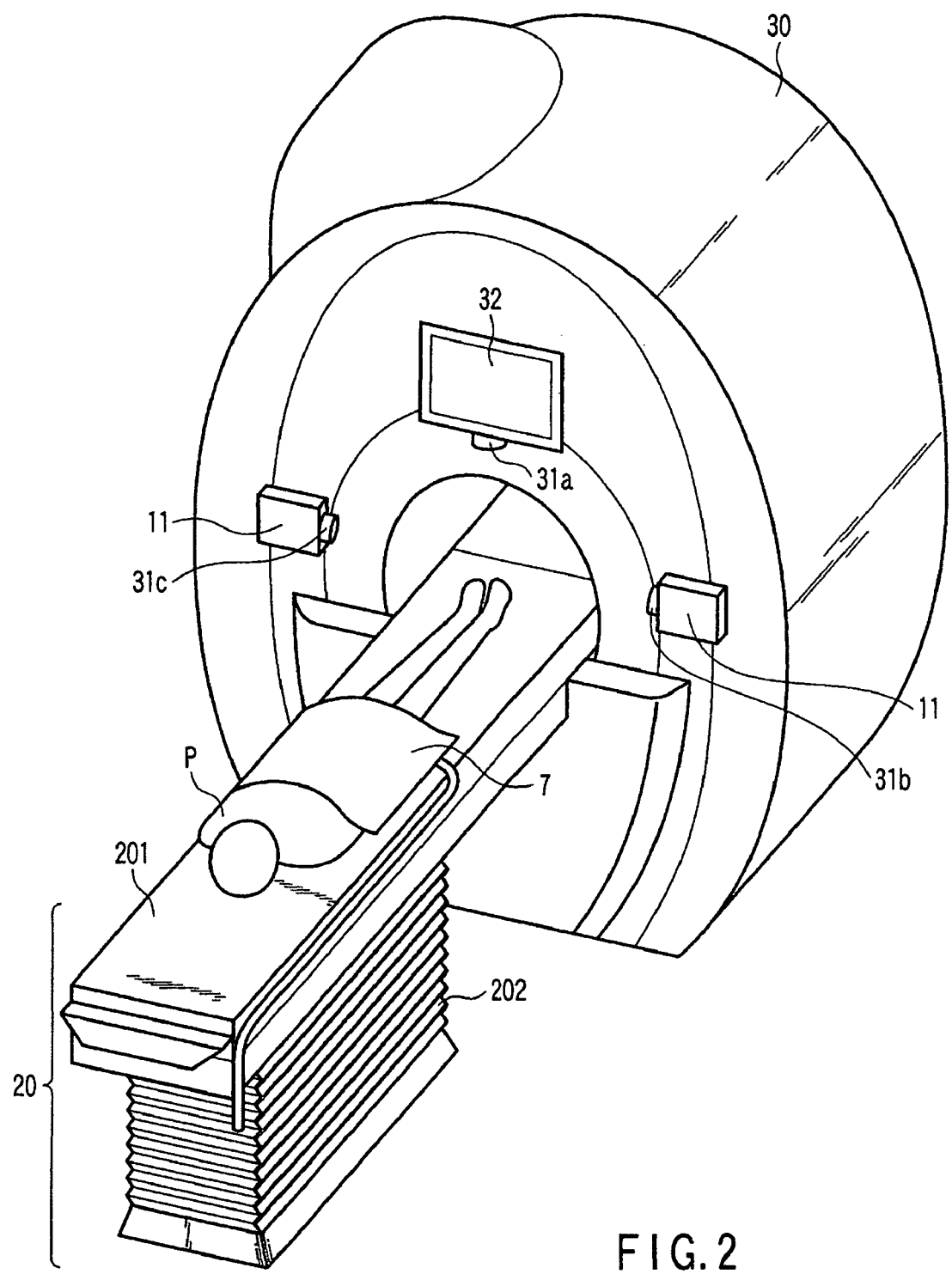
FIG. 2 is a perspective overhead view of the magnetic resonance imaging apparatus according to the embodiment.

FIG. 1 is a block configuration diagram of a magnetic resonance imaging apparatus according to an embodiment of the invention. FIG. 2 is a perspective overhead view of the magnetic resonance imaging apparatus. As shown in the diagrams, the magnetic resonance imaging apparatus includes: a bed 20 on which a patient P as a subject is mounted; a gantry 30 having a magnetostatic field generator for generating magnetostatic fields and a gradient magnetic field generator for adding position information to the magnetostatic fields; a transmitter/receiver for transmitting/receiving an RF signal; a controlling/computing unit for controlling the entire system and reconstructing an image; a biological information obtaining unit for obtaining signals indicative of waveforms of a respiration period of the subject P and ECG waveforms; a breath-hold instructing unit for instructing the patient P to hold his/her breath; and a support information obtaining/providing unit for obtaining and providing setting support information (which will be described later) for supporting a setting of a patient and an RF coil.

The magnetostatic field generator includes a magnet 1 of, for example, a superconductive type and a magnetostatic field power source 2 for supplying current to the magnet 1, and generates a magnetostatic field $B_0$ in an axial direction of a cylindrical opening (Z-axis direction) in which the subject P is placed. The space in the opening of the magnetostatic field $B_0$ in which the subject P is placed will be called "magnetostatic field space S" hereinbelow. A shim coil 14 is provided in the magnet part. To the shim coil 14, current for magnetostatic field equalization is supplied from a shim coil power source 15 under the control of a host computer which will be described later.

The bed 20 has a top board 201 and a top board driving unit 202. The subject P is placed on the top board 201 with the orientation and posture adapted to an image diagnosis. The top board 201 is vertically movable or, horizontally movable in the longitudinal direction, by the driving of the top board driving unit 202. By the horizontal movement of the top board 201, the subject P mounted on the top board 201 is placed in the magnetostatic field space in the magnet 1.

The gradient magnetic field generator includes a gradient coil unit 3. The gradient coil unit 3 has three sets of coils 3x, 3y, and 3z for generating gradient magnetic fields in the X-axis, Y-axis, and Z axis directions which are orthogonal to each other.

The gradient magnetic field generator also includes a gradient magnetic field power source 4 for supplying current to the coils 3x, 3y, and 3z. The gradient magnetic field power source 4 supplies pulse current for generating the gradient magnetic field to the coils 3x, 3y, and 3z under the control of a sequencer 5 which will be described later.

By adjusting the pulse current supplied from the gradient magnetic field power source 4 to the coils 3x, 3y, and 3z and combining the gradient magnet fields in the X-axis, Y-axis, and Z-axis directions as physical axes, each of logical axis directions of a slice-direction gradient magnetic field Gs, a phase encoding direction gradient magnetic field Ge, and a reading direction (frequency encoding direction) gradient magnetic field Gr which are orthogonal to each other can be arbitrarily set. The gradient magnetic fields in the slice direction, the phase encoding direction, and the reading direction are superimposed on the magnetostatic field $B_0$.

The transmitter/receiver includes an RF coil (radio frequency coil) V disposed on the surface of the subject P or near the subject P in the image acquisition space in the magnet 1, and a transmitter 8T and a receiver 8R connected to the coil 7. The transmitter 8T and the receiver 8R operate under the control of the sequencer 5 which will be described later. The transmitter 8T supplies an RF pulse of the Larmor frequency for causing nuclear magnetic resonance (NMR) to the RF coil 7. The receiver 8R takes an echo signal (high frequency signal) received by the RF coil 7, performs various signal processes such as pre-amplification, intermediate frequency conversion, phase detection, low-frequency amplification, and filtering on the echo signal, and then performs A/D conversion on the processed signal, thereby generating echo data (raw data) of a digital amount corresponding to the echo signal.

The controlling/computing unit includes the sequencer (also called sequence controller) 5, a host computer 6, a computing unit 10, a storing unit 11, a display 12, an input unit 13, and a sound generator 16. The host computer 6 has the function of instructing pulse sequence information to the sequencer 5 and controlling the operation of the whole apparatus in a centralized manner in accordance with a stored software procedure.

The host computer 6 statically or dynamically controls the components by controlling the operation of the magnetic resonance imaging apparatus in a centralized manner. In particular, the host computer 6 executes, in a subject/coil setting support function which will be described later, calculation of the position of a virtual magnetic field center, calculation for associating the position of the virtual magnetic field center and a setting image (which will be described later), a control on acquisition, storage, reading, and display of setting support information at predetermined timings, a movement control of moving the top board 201 for moving a designated imaging region to the virtual magnetic field center, and the like.

The sequencer 5 has a CPU and a memory. For example, the sequencer 5 stores pulse sequence information of non-radiographic MPA sent from the host computer 6, controls the operations of the gradient magnetic field power source 4, the transmitter 8T, and the receiver 8R in accordance with the information, temporarily receives the echo data output from the receiver 8R, and transfers the echo data to the computing unit 10. The pulse sequence information is all of information necessary for operating the gradient magnetic field power source 4, the transmitter 8T, and the receiver 8R in accordance with a series of pulse sequences. The pulse sequence information includes, for example, information on the intensity of pulse current applied to the coils $3x$, $3y$, and $3z$, application time, application timing, and the like.

The computing unit 10 receives the echo data which is output from the receiver 8R via the sequencer 5. The computing unit 10 places the echo data in a Fourier space (also called k space or frequency space) on an internal memory thereof and reconstructs the echo data to image data in a real space by two-dimensional or three-dimensional Fourier transform set by set. The computing unit can also perform a process of synthesizing data of an image, a difference computing process, and the like as necessary.

The synthesizing process includes an adding process of adding image data of a plurality of two-dimensional frames on a corresponding pixel unit basis, a maximum intensity projection (MIP) process and a minimum intensity projection process for selecting the maximum value and the minimum value, respectively, in the visual line direction in three-dimensional data, and the like. As another example of the synthesizing process, axes of a plurality of frames are adjusted to match each other in the Fourier space and echo data may be combined to echo data of one frame. The adding process includes a simple adding process, an averaging process, a weighted adding process, and the like.

The storing unit 11 can store not only reconstructed image data but also image data subjected to the synthesizing process or difference process. The storing unit 11 stores generated setting support information together with accompanying information such as subject ID, imaging region, test name, and series ID, for example, on the series unit basis. As necessary, a key image and a positioning image used for a certain image diagnosis may be stored so as to be included in an object which is shared to be used in another test.

The display 12 displays an image under the control of the host computer 6.

The input unit 13 is an I/F for inputting information related to imaging parameters desired by an operator, a pulse sequence, image synthesis, and difference computation to the host computer 6.

The sound generator 16 is provided as an element of the breath-hold instructing unit. The sound generator 16 can generate messages of breath-hold start and breath-hold end as voice messages under the control of the host computer 6.

The biological information obtaining unit has a biological information detecting unit 17 for detecting a signal indicative of the waveform of respiration of the subject, an ECG waveform, and the like, and a biological information transmitting unit 18 for outputting the detected biological information to the host computer 6 and the sequencer 5. The obtained biological information is used by the sequencer 5 at the time of executing an imaging scan. As a result, a respiration synchronizing timing by the respiration synchronizing method, and the like can be properly set. By performing an imaging scan based on the synchronization timing, data can be collected.

The support information obtaining/providing unit has a setting camera 31 and a setting monitor 32.

Figure 3:
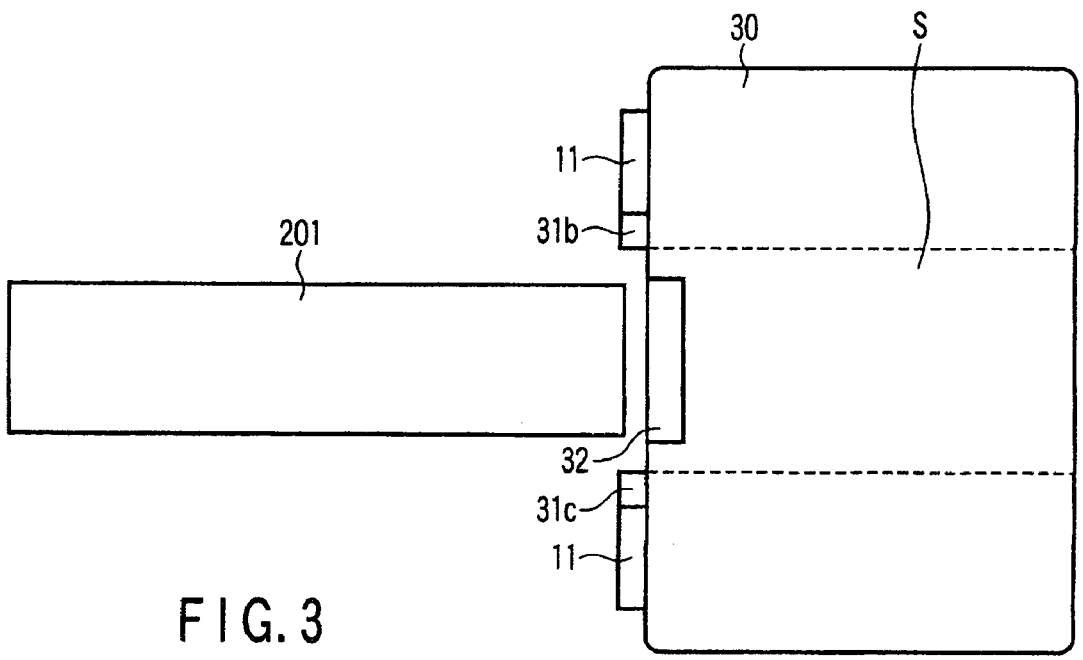
FIG. 3 is a diagram showing a configuration of installing a setting camera 31 and a setting monitor 32.

FIG. 3 is a diagram showing a configuration of mounting the setting camera 31 and the setting monitor 32. As shown in FIGS. 2 and 3, the setting camera 31 has an upper-side camera 31*a*, a right-side camera 31*b*, and a left-side camera 31*c* provided on the upper side, the right side, and the left side, respectively, of the gantry opening. By the cameras, images of the subject mounted on the top board 201 and the RF coil 7 on the surface of the subject or near the subject are acquired. The acquired images are displayed as setting images on the setting monitor 32. The setting images are images for showing a setting configuration of the subject P placed on the top board 201 and a setting configuration of the RF coil 7 placed on the surface of the subject P or near the subject P, on the outside of the magnetostatic field space.

The setting monitor 32 displays, together with the setting image, a virtual magnetic field center as a marker, for example, on the setting image, The virtual magnetic field center is a position outside of the magnetostatic field space S corresponding to the position of the magnetic field center (the center position of the magnetostatic field: isocenter) when the top board 201 is moved into the magnetostatic field space S. The position of the virtual magnetic field center can be calculated from the relation between the reference position of the top board 201 and the magnetic field center position in the magnetostatic field space S. The positional correspondence between the setting image and the virtual magnetic field center can be specified by calculating space coordinates of the virtual magnetic field center in the image capturing ranges of the cameras.

Further, the setting monitor 32 has a touch panel function for designating an imaging region on the displayed setting image.

In the examples of FIGS. 2 and 3, the monitor 32, the upper-side camera 31*a*, the right-side camera 31*b*, and the left-side camera 31*c* are disposed around the opening in the gantry 30. However, such an installation configuration is just an example. That is, the upper-side camera 31*a*, the right-side camera 31*b*, and the left-side camera 31*c* may be installed in other places as long as a preferable setting image can be acquired. The monitor 32 can be also installed in another place (such as the ceiling or wall of an image capturing room) as long as the operator can observe a setting image excellently. Further, in the example of FIGS. 2 and 3, the storing unit 11 is provided integrally with the right-side camera 31*b*, the left-side camera 31*c*, and the like. However, such a configuration of the storing unit 11 is just an example. For example, the storing unit 11 may be installed in a console of an operation room or the like.

(Subject/Coil Setting Support Function)

Next, the subject/coil setting support function of the magnetic resonance imaging apparatus will be described. The function is to support a setting of the subject or the coil by providing the subject/coil setting support information (hereinbelow, simply called "setting support information" or "support information"). The setting support information is information including at least an image (setting image) showing a configuration of setting a subject on the bed and a configuration of setting the RF coil for the subject. The setting support information also includes, as necessary, the position of a virtual magnetic field center on the setting image. The position of the virtual magnetic field center is displayed, for example, as a marker on the setting image.

Figure 4:
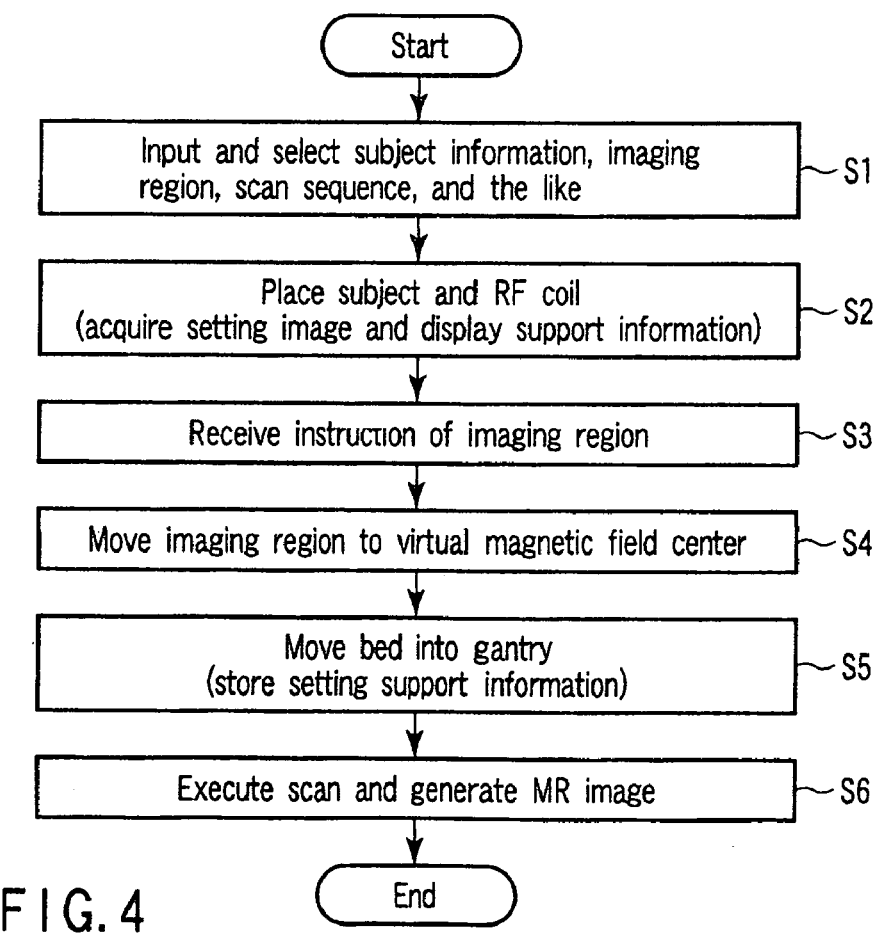
FIG. 4 is a flowchart showing the flow of an MR image obtaining process using a subject/coil setting support function according to a first embodiment.

FIG. 4 is a flowchart showing the flow of an MR image acquiring process using the subject/coil setting support function. As shown in FIG. 4, first, patient information, a region to be diagnosed, a scan sequence used for imaging, and the like are input from the input unit 13 and selected (step S1).

Next, a process of placing the subject P on the top board 201 and a process of placing the RF coil 7 on the subject P are executed (step S2). Specifically, in the process of placing the subject P and the RF coil 7, the setting camera 31 acquires a setting image showing the present locations of the subject P and the RF coil 7. The setting monitor 32 displays, as setting support information, the acquired setting image and the virtual magnetic field center on the image in real time. The operator sets the RF coil 7 and the like according to the purpose of a test (imaging region) while recognizing the position and the like by observing the setting support information displayed.

Figure 5A:
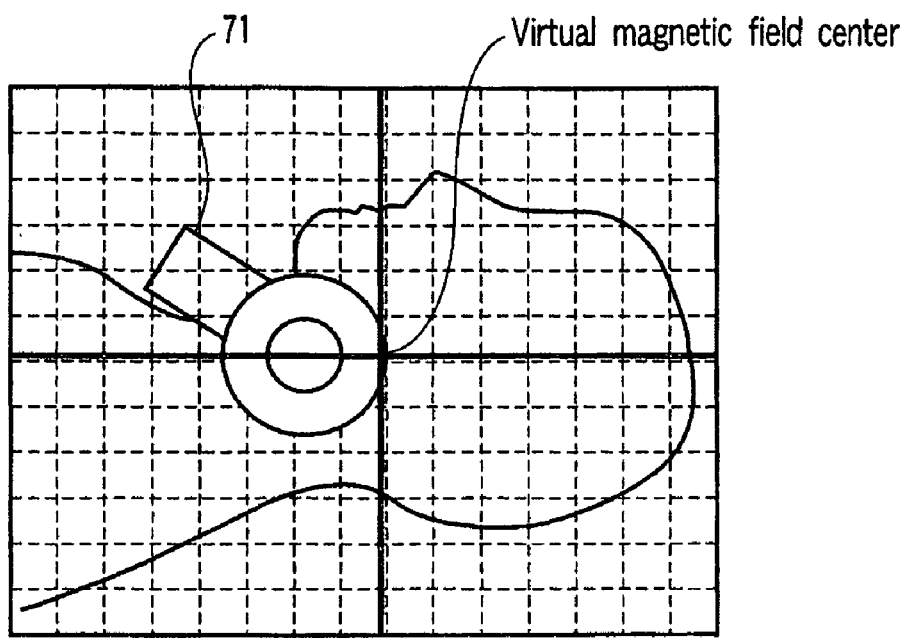
FIGS. 5A and 5B show an example of setting support information including a setting image acquired by a right-side camera 31b and the position of a virtual magnetic field center.

The setting images acquired by the upper-side camera 31a, the right-side camera 31b, and the left-side camera 31c can be arbitrarily selected to be displayed by a switching operation from the input unit 13. FIG. 5A shows an example of the setting support information including a setting image (using a local coil 71 for chin as an RF coil) acquired by the right-side camera 31b and the position of the virtual magnetic field center. The operator can grasp how much the center position of the local coil 71 for chin (that is, the imaging region) is apart from the virtual magnetic field center at present by observing the displayed setting support information.

Figure 5B:
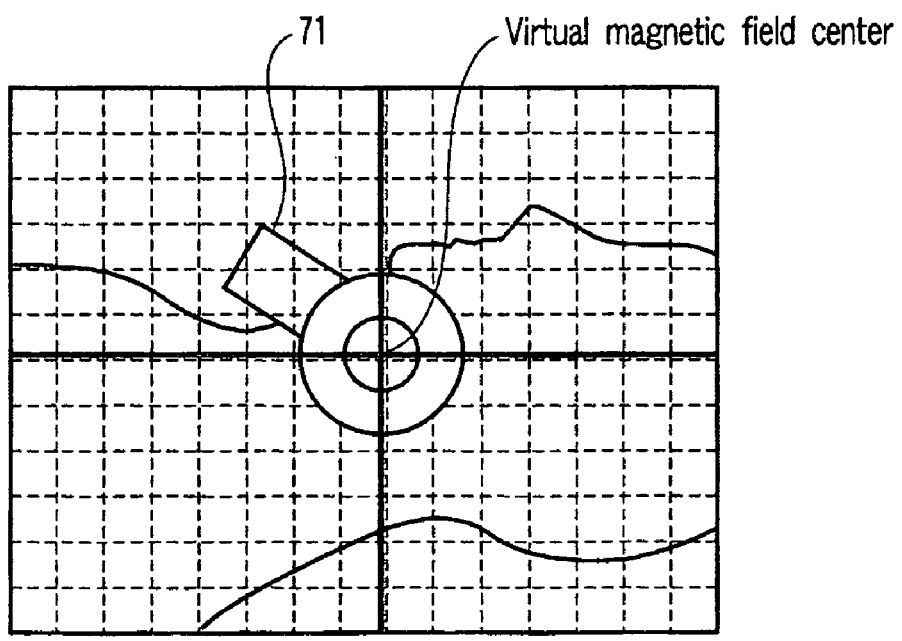

The operator touches the position on the setting image corresponding to the imaging region so that the instruction of the imaging region using the setting monitor 32 is accepted (step S3). The host computer 6 calculates the distance between an actual imaging region and the virtual magnetic field center by using the distance between the imaging region on the image (on the screen) and the virtual magnetic field center and a predetermined calculation formula. Alternatively, a table showing the correspondence of the distance between the imaging region on an image and the virtual magnetic field center and the distance between an actual imaging region and the virtual magnetic field center is pre-stored in the storing unit 11. With reference to the table, the distance between the actual imaging region and the virtual magnetic field center may be obtained from the distance between the imaging region on the image and the virtual magnetic field center. Further, the host computer 6 adjusts the imaging region to the virtual magnetic field center by moving the top board 201 vertically and horizontally in accordance with the distance between the actual imaging region and the virtual magnetic field center obtained by calculation (step S4). As a result of the positioning, for example, the center (that is, the imaging region) of the local coil 71 or chin shown in FIG. 5A substantially coincides with the virtual magnetic field center as shown in FIG. 5B.

In the above example, the case has been described in which the distance between the actual imaging region and the virtual magnetic field center is calculated on the basis of a position designation on the monitor 32 and, on the basis of the result, the apparatus moves the top board 201, thereby automatically performing positioning between the imaging region and the virtual magnetic field center. The present invention, however, is not limited to the example. For example, the operator may perform positioning between the imaging region and the virtual magnetic field center by moving the top board 201 by a manual operation while observing the imaging region and the virtual magnetic field center displayed. Further, the automatic positioning performed by the apparatus and the positioning performed by the manual operation may be combined.

When an instruction of loading the top board 201 is entered from the input unit 13, the host computer 6 moves the top board 201 in the horizontal direction to load the subject P into the magnetostatic field space S. Using an input instruction of loading the top board 201 as a trigger, the host computer 6 stores the setting support information displayed on the setting monitor 32 into the storing unit 11 (step S5). The timing of storing the setting support information displayed is not limited to the timing of receiving the instruction of loading the top board 201. For example, the operator may directly enter the storing instruction by a manual operation. Any configurations of storing/managing setting support information may be employed. As a typical example, setting support information may be stored and managed so as to be associated with a series UID (Unique IDs) of images collected by using the support information. Alternatively, the setting support information may be stored and managed so as to be associated with a positioning image or the like as an object used as shared information.

After that, the sequencer 5 executes an imaging scan in accordance with a predetermined sequence. The computing unit 10 reconstructs an image using an MR signal obtained by imaging and generates an MR image. The generated MR image is displayed in a predetermined form on the display 12 and, as necessary, stored in the storing unit 11 (step S6).

(Effects)

With the configuration described above, the following effects can be obtained.

The magnetic resonance imaging apparatus displays support information including at least a setting image showing a configuration of placing a patient on a bed and a configuration of placing an RF coil for the patient at present. As necessary, the support information may include the position of a virtual magnetic field center corresponding to the magnetic field center position in the case where the bed is moved into the gantry. By observing the displayed support information, the operator can promptly and easily determine whether the present configurations of placing the patient and the RF coil are proper or not, and can accurately correct the configuration of placing the patient or the RF coil. As a result, the work load on the operator with respect to the setting of the patient and the RF coil can be reduced as compared with that in the conventional technique, and the invention can contribute to improvement in the quality of a diagnosis image and stability.

In the magnetic resonance imaging apparatus, by designating an imaging region on a setting image displayed on a monitor screen, an actual distance between the imaging region and the virtual magnetic field center is computed, and the bed is moved so that an imaging region designated on the basis of the computation result and the virtual magnetic field center coincide with each other. The operator can realize positioning between an imaging region and the virtual magnetic field center only by designating the imaging region displayed on the monitor screen. Therefore, the work load on the operator with respect to the setting of a patient and an RF coil can be reduced. The movement of a patient on the bed for positioning between an imaging region and the virtual magnetic field center can be minimized, so that the load on the patient in image diagnosis can be also reduced.

Further, the support information used for setting a subject and an RF coil is stored in the storing unit in response to a predetermined trigger. Therefore, the operator can accurately and easily reproduce the setting of the same subject and RF coil by using the stored support information.

Second Embodiment

A second embodiment of the present invention will now be described. In the second embodiment, as the setting support information, not only the present setting image and the virtual magnetic field center but also setting support information in the past (for example, only a setting image) are displayed simultaneously (for example, superimposition display, parallel display, or the like) or alternately.

Figure 6:
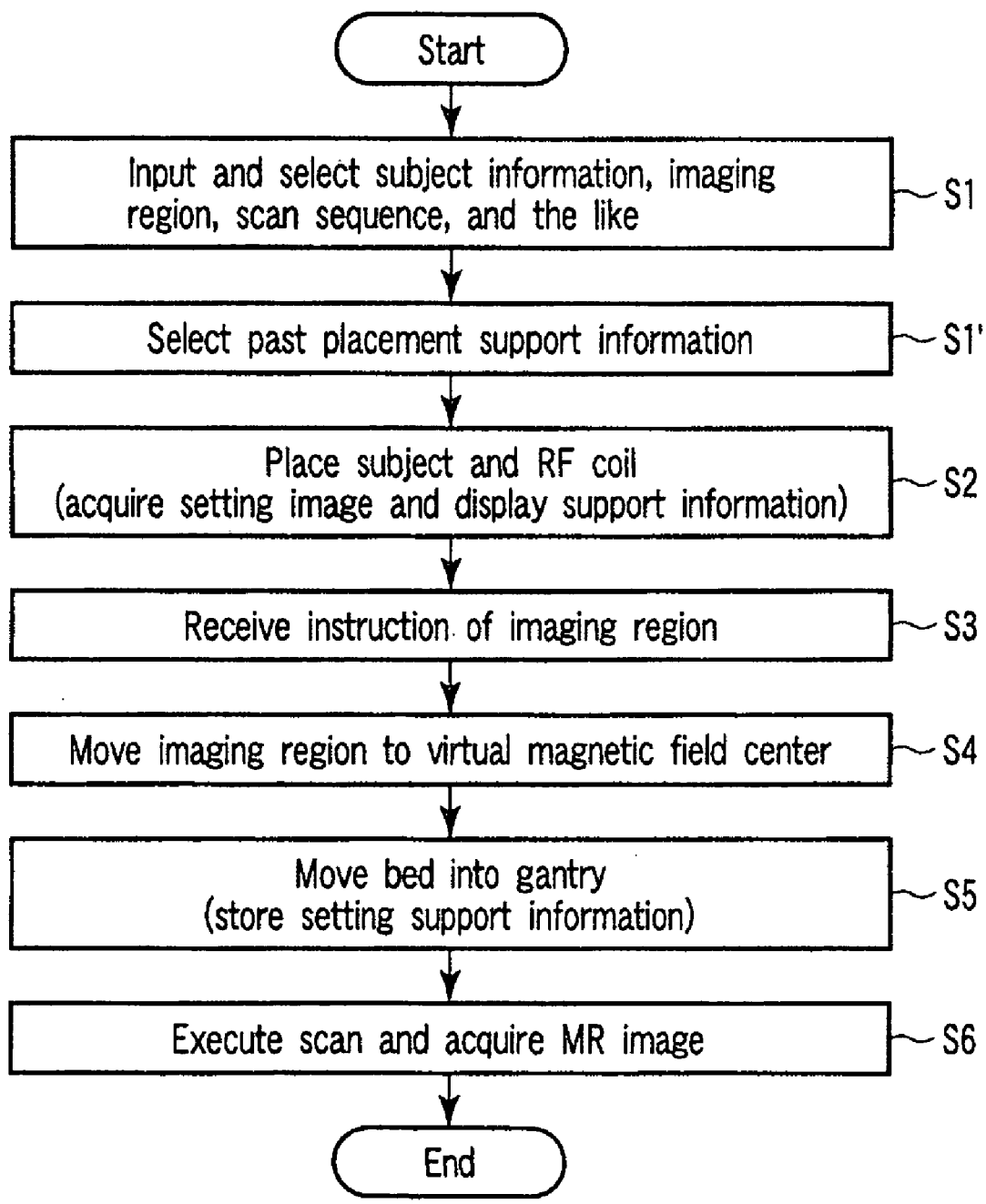
FIG. 6 is a flowchart showing the flow of an MR image obtaining process using a subject/coil setting support function according to a second embodiment.

FIG. 6 is a flowchart showing the flow of an MR image acquiring process using a subject/coil setting support function according to the second embodiment. As shown in the diagram, first, patient information, a region to be diagnosed, a scan sequence to be used for imaging, and the like are input from the input unit 13 and selected (step S1).

Next, setting support information in the past is selected (step S1'). Specifically, setting support information in the past which is obtained with respect to the subject is selected on the basis of image acquisition date, subject ID, series ID, and the like. In the second embodiment, to make the description concrete, it is assumed that setting support information in the past of the same subject is selected. The invention, however, is not limited to the selection. For example, setting support information obtained in a past image diagnosis by a doctor or technician of high technical capability may be selected.

Next, a process of placing the subject P on the top board 201 and a process of placing the RF coil 7 for the subject P are executed (step S2). Simultaneously, setting support information including a present setting image, a past setting image, and a virtual magnetic field center is displayed on the setting monitor 32. The operator sets the RF coil 7 and the like according to a test purpose (imaging region) while seeing the positions and the like so that the placement of the subject P and the RA coil 7 on the past setting image and that of the subject P and the RF coil 7 on the present setting image coincide with each other.

Subsequently, the operator touches the position on the setting image corresponding to the imaging region so that the instruction of the imaging region using the setting monitor 32 is accepted (step S3). The host computer 6 calculates the distance between an actual imaging region and the virtual magnetic field center in response to the instruction of the imaging region. According to the result of the calculation, the host computer 6 adjusts the imaging region to the virtual magnetic field center by moving the top board 201 vertically and horizontally (step S4).

When an instruction of loading the top board 201 is entered from the input unit 13, the host computer 6 moves the top board 201 in the horizontal direction to load the subject P into the magnetostatic field space. When the instruction of loading the top board 201 is received, the host computer 6 stores the setting support information displayed on the setting monitor 32 into the storing unit 11 (step S5). The setting support information to be stored does not always have to include a past setting image used for reference. As necessary, in place of entity data of a past setting image, information that specifies the location of the past setting image may be included in additional information of the setting support information.

After that, the sequencer 5 executes an imaging scan in accordance with a predetermined sequence. The computing unit 10 performs image reconstruction using an MR signal obtained by imaging to generate an MR image. The generated MR image is displayed in a predetermined form on the display 12 and, as necessary, stored in the storing unit 11 (step S6).

(Effects)

The magnetic resonance imaging apparatus can display a past setting image and a present setting image simultaneously or alternately. By observing a displayed past setting image and doing the same as the setting configuration, the operator can accurately and easily reproduce the same patient placement or coil placement as that in the past. As a result, the work load on the operator with respect to the setting of the patient and the RF coil can be reduced as compared with that in the conventional technique, and the invention can contribute to improvement in the quality of a diagnosis image and stability in quality. The effect is particularly conspicuous when imaging is performed to see the course of a treatment.

The present invention is not limited to the foregoing embodiments but can be embodied by modifying the components without departing from the gist of the present invention at a stage of carrying out the invention. Concrete examples of modifications are as follows.

(1) The functions according to the embodiments can be also realized by installing a program that executes the process into a computer such as a workstation and developing the program on a memory. A program that can cause a computer to execute the method can be stored on a recording medium such as a magnetic disk (floppy (registered trademark) disk, hard disk, or the like), an optical disk (CD-ROM, DVD, or the like), or a semiconductor memory and distributed.

(2) In the foregoing embodiments, the case of biological information synchronization such as respiration has been described as an example. However, in the magnetic resonance imaging apparatus, the biological information synchronization function is not essential. For example, in the case of acquiring images of the head, four limbs, and the liker imaging using the non-radiographic MRA function or the like can be performed without using respiration synchronization and electrocardiograph synchronization.

(3) In the case where the placement of a subject or RF coil in the same kind of a test in the past is changed in the magnetic resonance imaging, it is preferable to record, together with the information of the changer at least one of support information before the change and support information after the change as protocol change history information.

(4) In the foregoing embodiments, the case of the magnetic resonance imaging apparatus has been described as an example. The present invention, however, is not limited to the magnetic resonance imaging apparatus. The technical idea of the present invention can be also applied to a computerized traverse axial tomography apparatus, a nuclear medicine diagnostic apparatus, an X-ray diagnostic apparatus, and the like requiring placement of a subject on a bed top board.

(5) In the foregoing embodiments, the setting support information including a setting image and the position of a virtual magnetic field center has been described as an example. The setting support information may also include other information. For example, when a connector of the RF coil 7 is connected to the apparatus, the type of the connector may be obtained and included in the setting support information. The type of the RF coil 7 included in the setting support information can be also displayed in a predetermined form together with the setting image.

(6) In the foregoing embodiments, the case of the non-radiographic MRA imaging has been described as an example. The present invention, however, is not limited to the non-radiographic MRA imaging. The technical idea of the present invention can be also applied to a conventional imaging (for example, T1 weighted imaging, T2 weighted imaging, proton density imaging and the like), radiographic MRA imaging, a cine imaging, a diffusion-weighted imaging and the like.

By properly combining the plurality of components disclosed in each of the embodiments, various inventions can be generated. For example, some components may be deleted from all of the components disclosed in each of the embodiments. Further, the components in the different embodiments may be properly combined.

What is claimed is:

1. A magnetic resonance imaging apparatus comprising:
a gantry which generates a magnetostatic field space;
a bed which places a subject placed on a top board on the outside of the magnetostatic field space into the magnetostatic field space by moving the top board;
an RF coil disposed on a surface of the subject or near the subject;
an image capturing unit which acquires a setting image for showing a setting configuration of the subject placed on the top board on the outside of the magnetostatic field space and a setting configuration of the RF coil placed on the surface of the subject or near the subject;
a support information generating unit which generates support information including at least the setting image and supporting at least one of a setting of the subject onto the top board and a setting of the RF coil; and
a display unit which displays the support information.

2. The magnetic resonance imaging apparatus according to claim 1, wherein the support information generating unit generates the support information including a virtual magnetic field center as a position on the outside of the magnetostatic field space corresponding to a magnetic field center position in the case where the top board is moved into the magnetostatic field space.

3. The magnetic resonance imaging apparatus according to claim 1, further comprising:
a designating unit which designates an imaging region in the subject placed on the top board on the outside of the magnetostatic field space; and
a control unit which controls the bed mechanism so that the designated imaging region is moved to the virtual magnetic field center.

4. The magnetic resonance imaging apparatus according to claim 1, wherein the designating unit is a touch panel using the display unit.

5. The magnetic resonance imaging apparatus according to claim 1, further comprising a storing unit which stores the support information.

6. The magnetic resonance imaging apparatus according to claim 5, further comprising a control unit which controls a timing of storing the support information using, as a reference, a timing of moving the top board on the outside of the magnetostatic field space into the magnetostatic field space.

7. The magnetic resonance imaging apparatus according to claim 5, wherein the storing unit stores a positioning image used for a certain image diagnosis and a diagnosis image used as a basis of a diagnosis so as to be included in or associated with an object which is shared to be used for another image diagnosis.

8. The magnetic resonance imaging apparatus according to claim 1, wherein the display unit displays the setting image generated in the past and the present setting image support information simultaneously or alternately.

9. The magnetic resonance imaging apparatus according to claim 1, wherein the display unit is provided on the bed side of the gantry.

10. A magnetic resonance imaging apparatus comprising:
a gantry having an opening into which a subject is inserted, a magnetostatic field magnet which generates a magnetostatic field space, and a gradient coil which generates a gradient magnetic field;
a bed which inserts a top board on which the subject is mounted into the opening;
an RF coil disposed on a surface of the subject or near the subject;
an image capturing unit which acquires an image of the subject including the RF coil;
a support information generating unit which generates a setting image showing a positional relation between the subject and the RF coil on the basis of information acquired by the image capturing unit in order to support a setting of the RF coil to the subject; and
a display unit which displays the setting image.

11. The magnetic resonance imaging apparatus according to claim 10, wherein the support information generating unit also generates support information for supporting a setting of the subject on the top board, and
the display unit displays the support information together with the setting image.

12. A setting supporting apparatus for use in a magnetic resonance imaging apparatus which applies a uniform magnetostatic field to a subject, applies a high frequency magnetic field and a gradient magnetic field in accordance with a predetermined pulse sequence, and detects a magnetic resonance signal from the subject by an RF coil to acquire an image, the setting supporting apparatus comprising:
an image capturing unit which acquires an image of the subject including the RF coil;
a support information generating unit which generates a setting image showing a positional relation between the subject and the RF coil on the basis of information acquired by the image capturing unit in order to support a setting of the RF coil to the subject; and
a display unit which displays the setting image.

13. The setting supporting apparatus according to claim 12, wherein the support information generating unit also generates support information for supporting a setting of the subject on the top board, and
the display unit displays the support information together with the setting image.

14. A method of supporting a setting of an RF coil to a subject in magnetic resonance imaging, comprising:
capturing an image of the subject mounted on a top board of a bed and an RF coil disposed on a surface of the subject or near the subject;
generating a setting image showing a positional relation between the subject and the RF coil on the basis of information acquired by the image capturing in order to support the setting of the RF coil to the subject; and
displaying the setting image.

15. A method of supporting a setting of an RF coil to a subject in magnetic resonance imaging, comprising:
capturing an image of the subject mounted on a top board of a bed and an RF coil disposed on a surface of the subject or near the subject;
generating a setting image showing a positional relation between the subject and the RF coil on the basis of information acquired by the image capturing in order to support the setting of the RF coil to the subject;
generating support information for supporting a setting of the subject on the top board; and
displaying the support information together with the setting image.

* * * * *